(12) United States Patent
Gupta et al.

(10) Patent No.: US 8,408,860 B2
(45) Date of Patent: Apr. 2, 2013

(54) METHOD AND APPARATUS FOR ORIENTATING A SOLID GROWTH CULTURE MEDIUM PLATE

(75) Inventors: Rajiv Gupta, Cupertino, CA (US);
Stephen Lewis Leckenby, Victoria (CA); Phillip James Duncan, Mount Waverley (AU); Daniel Patrick Torpy, Surrey Hills (AU); Colin William Potter, Nunawading (AU)

(73) Assignee: Labtech Systems Limited, Adelaide, South Australia ( * ) Notice: Subject to any disclaimer, the term of this patent is extended or adjusted under 35 U.S.C. 154(b) by 751 days.

(21) Appl. No.: 12/520,972

(22) PCT Filed: Jan. 11, 2008

(86) PCT No.: PCT/AU2008/000017
§ 371 (c)(1),
(2), (4) Date: Dec. 14, 2009

(87) PCT Pub. No.: WO2008/083440
PCT Pub. Date: Jul. 17, 2008

(65) Prior Publication Data
US 2010/0172735 A1 Jul. 8, 2010

(30) Foreign Application Priority Data

Jan. 12, 2007 (AU) .............................. 2007900145

(51) Int. Cl.
*B65B 25/00* (2006.01)
*A22C 7/00* (2006.01)

(52) U.S. Cl. .......... 414/411; 414/783; 53/381.4; 53/109
(58) Field of Classification Search .................. 414/405, 414/411, 419, 420, 421, 425, 754, 758, 763, 414/771, 773, 776, 783; 53/109, 381.1, 381.4, 53/468, 471, 76
See application file for complete search history.

(56) References Cited

U.S. PATENT DOCUMENTS

| 1,956,192 | A | * | 4/1934 | Donnelly | .................. 425/174.6 |
| 3,455,788 | A | | 7/1969 | Curry et al. | |
| 3,513,621 | A | * | 5/1970 | Chamberlin | ..................... 53/468 |
| 3,623,958 | A | | 11/1971 | Fitzgerald et al. | |
| 3,632,478 | A | | 1/1972 | Fink | |
| 3,660,243 | A | | 5/1972 | Young | |
| 3,777,455 | A | * | 12/1973 | Allen | ........................... 53/381.4 |

(Continued)

FOREIGN PATENT DOCUMENTS

| CA | 1286621 C | 7/1991 |
| DE | 19520420 C2 | 12/1996 |

(Continued)

*Primary Examiner* — Gregory Adams
(74) *Attorney, Agent, or Firm* — Seager, Tufte & Wickhem LLC

(57) ABSTRACT

An apparatus for orientating a solid growth culture medium plate from an original orientation to a worked orientation, the plate having a lid and a bottom, the apparatus including an orientation mechanism that includes opposed jaws able to receive and hold a plate therebetween in a held position that defines a notional tube above and below the plate, the orientation mechanism being mounted on a jaw support member such that the jaw support member is rotatable such that at least the plate bottom rotates about a generally horizontal axis that intersects the notional tube to orientate at least the plate bottom from the original orientation to the worked orientation.

21 Claims, 5 Drawing Sheets

U.S. PATENT DOCUMENTS

| | | | |
|---|---|---|---|
| 3,778,351 A | | 12/1973 | Rosov |
| 3,788,951 A | | 1/1974 | von der Pfordten |
| 3,799,844 A | | 3/1974 | Campbell et al. |
| 3,830,701 A | | 8/1974 | Stussman et al. |
| 3,850,754 A | | 11/1974 | Wilkins et al. |
| 3,935,075 A | | 1/1976 | Perry et al. |
| 3,962,040 A | | 6/1976 | Campbell et al. |
| 4,002,093 A | * | 1/1977 | Heisler ............................ 83/154 |
| 4,010,077 A | | 3/1977 | Pardos |
| 4,102,748 A | | 7/1978 | Vacanti |
| 4,144,135 A | | 3/1979 | Sequeira |
| 4,170,861 A | | 10/1979 | Snyder et al. |
| 4,287,301 A | | 9/1981 | Astle |
| 4,613,573 A | | 9/1986 | Shibayama et al. |
| 4,687,746 A | | 8/1987 | Rosenberg et al. |
| 4,892,831 A | | 1/1990 | Wong |
| 4,921,387 A | * | 5/1990 | Bennington .................. 414/779 |
| 4,981,802 A | | 1/1991 | Wylie et al. |
| 5,020,297 A | | 6/1991 | Borie et al. |
| 5,048,259 A | * | 9/1991 | Cox et al. ...................... 53/132.1 |
| 5,106,584 A | | 4/1992 | Funakubo et al. |
| 5,206,171 A | | 4/1993 | Dillon et al. |
| 5,360,309 A | * | 11/1994 | Ishiguro ........................ 414/404 |
| 5,609,717 A | * | 3/1997 | Pascale et al. ................. 156/556 |
| 5,629,201 A | | 5/1997 | Nugteren et al. |
| 5,691,195 A | | 11/1997 | Doleans et al. |
| 5,695,988 A | | 12/1997 | Chong |
| 5,756,304 A | | 5/1998 | Jovanovich |
| 6,291,234 B1 | | 9/2001 | Raz et al. |
| 6,398,008 B1 | * | 6/2002 | Suga ............................ 198/404 |
| 6,521,190 B1 | | 2/2003 | Edens et al. |
| 6,617,146 B1 | | 9/2003 | Naccarato et al. |
| 6,843,962 B2 | | 1/2005 | Haslam et al. |
| 7,565,786 B2 | * | 7/2009 | Miksch ........................ 53/381.4 |
| 7,709,268 B1 | | 5/2010 | Edwards et al. |
| 2002/0064867 A1 | | 5/2002 | Clark et al. |
| 2002/0120214 A1 | | 8/2002 | Cole |
| 2007/0202564 A1 | | 8/2007 | Glasson et al. |
| 2008/0318310 A1 | | 12/2008 | Dufresne et al. |

FOREIGN PATENT DOCUMENTS

| | | |
|---|---|---|
| FR | 2668495 A1 | 4/1992 |
| GB | 2025457 A | 1/1980 |
| GB | 2247076 A | 2/1992 |
| GB | 2255407 A | 11/1992 |
| JP | 63-207377 A | 8/1988 |
| JP | 01191678 B | 8/1989 |
| JP | 02072898 A | 3/1990 |
| JP | 03049676 A | 3/1991 |
| JP | 03061476 A | 3/1991 |
| JP | 03133375 A | 6/1991 |
| JP | 03175996 A | 7/1991 |
| JP | 04234973 A | 8/1992 |
| JP | 04248980 A | 9/1992 |
| JP | 05225995 A | 9/1993 |
| JP | 05344535 A | 12/1993 |
| JP | 06225753 A | 8/1994 |
| JP | 06296481 A | 10/1994 |
| JP | 7-75551 A | 3/1995 |
| JP | 07067695 A | 3/1995 |
| JP | 07170970 A | 7/1995 |
| JP | 10004952 A | 1/1998 |
| JP | 10309199 A | 11/1998 |
| JP | 11346796 A | 12/1999 |
| JP | 2001149062 A | 6/2001 |
| JP | 2001149063 A | 6/2001 |
| JP | 2001153761 A | 6/2001 |
| JP | 2002098704 A | 4/2002 |
| JP | 3414431 B2 | 6/2003 |
| JP | 2005052069 A | 3/2005 |
| JP | 2006-335514 A | 12/2006 |
| JP | 2008166201 A | 7/2008 |
| WO | 8808024 A1 | 10/1988 |
| WO | 0166686 A1 | 9/2001 |
| WO | 2004022245 A1 | 3/2004 |

* cited by examiner

METHOD AND APPARATUS FOR ORIENTATING A SOLID GROWTH CULTURE MEDIUM PLATE

This international patent application claims priority from Australian provisional patent application 2007900145 filed on 12 Jan. 2007, the contents of which are to be taken as incorporated herein by this reference.

FIELD OF THE INVENTION

The present invention relates generally to apparatus involved in the inoculation of solid growth culture media with a microbiological sample, and the subsequent streaking of the inoculum to produce isolated bacterial colonies, principally for diagnostic purposes in a laboratory, such as medical diagnostic purposes. The present invention specifically relates to a method and an apparatus for orientating a solid growth culture medium plate, both before and after a streaking operation, in an automated streaking apparatus. However, the invention is not to be limited to only that application.

BACKGROUND OF THE INVENTION

The isolation of individual colonies of micro-organisms (and in particular bacteria) is an important procedure in many microbiological laboratories. Traditionally, this isolation of bacteria has been performed manually by skilled laboratory technicians who first dispense a microbiological sample onto the surface of a solid growth culture medium, such as agar in a Petri dish (which will hereafter simply be referred to as a "medium" in an "agar plate" or simply in a "plate"), followed by the use of a hand-tool to spread the sample across the surface of the medium (called "streaking").

The hand-tool typically includes a terminal loop to make multiple streaks of increasing dilution of the inoculum across the medium. The streaks of increasing dilution tend to provide, generally towards the tail of the streaks, a number of single cells that allow for the growth of isolated microbiological colonies after incubation. These isolated colonies may then be analysed for colony morphology, and may undergo staining and other procedures which are necessary for determining, for example, the genus, the species and the strain of the previously unidentified organism.

Traditionally, the normal laboratory handling regimes for such solid growth culture media plates sees the plates being stored before inoculation and streaking (hereafter referred to as "processing"), and also after processing, in an inverted orientation. By way of explanation, it is usual for solid growth culture medium plates to be stored upside-down such that their lids are facing downwardly and their bottoms (containing the agar) are stored uppermost. This is done to prevent any condensation that may form inside the lid from falling onto the medium surface, which would occur if the plates were not stored in an inverted orientation, thereby damaging the integrity of the medium and (after processing) the microbiological inoculum.

Inoculation and streaking of the type mentioned above is highly repetitious and in many pathology diagnostic microbiology laboratories is usually conducted in very high volumes, such as in volumes as high as 1,000 to 15,000 plates per day. It is tedious and laborious work that therefore is prone to error and inaccuracies. It is quite obviously work that would lend itself to either partial or full automation.

The literature is replete with suggestions for how best to automate these laboratory functions, yet very few of these suggestions have ever actually found success in a commercial laboratory environment. It therefore appears that the successful enablement of suitable laboratory apparatus has to date, for most, proved elusive.

Three recent suggestions for the automation of these laboratory functions can be found in the following documents; U.S. Pat. No. 4,981,802 (C. Wylie et al) titled "Method and Apparatus for Streaking a Culture Medium", U.S. Pat. No. 6,617,146 (F. Naccarato et al) titled "Method and Apparatus for Automatically Inoculating Culture Media With Bacterial Specimens From Specimen Containers", and international patent publication WO2005/071055 (Medvet Science Pty Ltd) titled "Microbial Streaking Device" (licensed to the present applicant).

The Wylie and Naccarato patents describe automated and semi-automated apparatus that utilize re-usable streaking tools similar to the hand streaking tools mentioned above, although only the Naccarato patent suggests that its apparatus is capable of orientating a plate from an inverted orientation prior to processing. In this respect, the Naccarato patent describes placing an inverted plate on a conveyor belt, gripping the (uppermost) bottom portion of the plate, and lifting that bottom portion off the lid and away from the belt with an arm that pivots about a horizontal axis that is adjacent to, and lies in the same plane as, the conveyor belt. This suggestion seems to require the lid to already be loose on the plate and is clearly likely to be imprecise and have a high failure rate. At the very least, it seems to be likely to give rise to a reasonably slow operation.

While the Medvet Science publication describes the use of a new form of streaking tool, being a streaking applicator that includes a line of spaced apart contact surfaces (for contact with the surface of solid growth media), the contact surfaces being resiliently flexibly supported by a common support member, it too does not describe an apparatus capable of orientating a plate from an already inverted orientation.

It is an aim of the present invention to provide both a method and an apparatus capable of orientating a solid growth culture medium plate, such as would be required prior to, and after, inoculation and streaking of that plate in a laboratory. In this respect, and as foreshadowed above, it is also an aim of the present invention for the method and apparatus to find use in laboratory situations other than the inoculation and streaking situations described above. Indeed, in its broadest form, the method and apparatus of the present invention may find use in any laboratory to simply provide an automated process of inverting solid growth culture medium plates, with or without lids, either before or after being loaded with agar, and either before or after storage.

Before turning to a summary of the present invention, it must be appreciated that the above description of the prior art has been provided merely as background to explain the context of the invention. It is not to be taken as an admission that any of the material referred to was published or known, or was a part of the common general knowledge in Australia or elsewhere.

It is also useful to provide an explanation of some of the terms that will be used to define the spatial relationship of the apparatus and various parts thereof. In this respect, spatial references throughout this specification will generally be based upon a plate ultimately being inoculated and streaked in an automated streaking apparatus in an upright orientation, with the surface of the medium in the plate being generally flat and horizontal (having previously been stored in an inverted orientation for the reasons mentioned above).

With this environment as the basis, the apparatus and some parts thereof may then be defined with reference to the "horizontal", allowing further references to "upper" or "upwardly"

and "lower" or "downwardly", and also to the "vertical". In this respect, the traditional geometric spatial reference to x, y and z dimensions, and then to the x direction (or axis), the y direction (or axis) and the z direction (or axis), will also be adopted, with the x and y directions lying generally horizontally and the z direction lying generally vertically.

Finally, some aspects of the present invention that may ultimately be claimed in isolation (and not in an in-use environment), may nonetheless be difficult to describe and understand in isolation. Thus, some of the following description does describe the invention and its embodiments in such an in-use environment (for example, in association with an automated streaking apparatus, or with reference to its use with an originally inverted plate). Of course, it must be appreciated that the use of such description, and the use of the abovementioned spatial relationships, to define the present invention, is not to be seen as a limitation and certainly is not to be seen as a limitation only to the in-use environment, unless that intention is clearly stated.

SUMMARY OF THE INVENTION

The present invention provides an apparatus for orientating a solid growth culture medium plate from an original orientation to a worked orientation, the plate having a lid and a bottom, the apparatus including an orientation mechanism that includes opposed jaws able to receive and hold a plate therebetween in a held position that defines a notional tube above and below the plate, the orientation mechanism being mounted on a jaw support member such that the jaw support member is rotatable such that at least the plate bottom rotates about a generally horizontal axis that intersects the notional tube to orientate at least the plate bottom from the original orientation to the worked orientation.

The present invention also provides a method for orientating a solid growth culture medium plate from an original orientation to a worked orientation, the plate having a lid and a bottom and, the method including the steps of:
 a) clamping a plate in its original orientation between opposed jaws mounted on a jaw support member of an orientation mechanism, thus forming a held position that defines a notional tube above and below the plate; and
 b) rotating at least the plate bottom about a generally horizontal axis that intersects the notional tube to orientate at least the plate bottom from the original orientation to the worked orientation.

In a preferred form of the present invention, the apparatus is not only able to orientate a plate from an original orientation to a worked orientation, but is also able to de-lid the plate either before, during or after the orientation. Ideally, one continuous movement will orientate the plate from the original orientation to the worked orientation and de-lid the plate. Also ideally, the apparatus is configured such that the orientation and the de-lidding are both able to occur substantially within the notional tube and thus in essentially the same vertical axis.

In one form, the apparatus will firstly rotate both the lid and the plate bottom, when in the held position, to orientate both from the original orientation to the worked orientation, following which the lid and plate bottom can be separated to de-lid the plate for subsequent processing of the plate bottom. However, in a preferred form, the apparatus will rotate only the plate bottom, leaving the lid retained in its original orientation, thus de-lidding and orientating in essentially one motion.

Thus, the present invention also provides an apparatus for orientating a solid growth culture medium plate from an original orientation to a worked orientation, the plate having a lid and a bottom, the apparatus including:
 an orientation mechanism that includes opposed jaws able to receive and hold a plate therebetween in a held position that defines a notional tube above and below the plate, one of the jaws including a plate-bottom gripping device and being rotatably mounted on a jaw support member such that the plate bottom rotates about a generally horizontal axis that intersects the notional tube to orientate the plate bottom from the original orientation to the worked orientation, the other jaw including a lid-gripping device that retains the lid in its original orientation during rotation of the plate bottom; and
 a plate platform having a plate clamping member able to receive, from the orientation mechanism, the plate bottom in its worked orientation.

In one form of the present invention, the plate bottom in its worked orientation will preferably lie below and underneath the retained lid (which will have been retained in its original orientation) and thus still lies generally within the notional tube. In this form, the de-lidding will also have occurred generally within the notional tube.

The present invention thus also provides a further method for orientating a solid growth culture medium plate from an original orientation to a worked orientation, the plate having a lid and a bottom, the method including the steps of:
 a) clamping a plate in its original orientation between opposed jaws, one of the jaws including a plate-bottom gripping device rotatably mounted on a jaw support member of an orientation mechanism, thus forming a held position that defines a notional tube above and below the plate, the other jaw including a lid-gripping device;
 b) rotating the plate bottom about a generally horizontal axis that intersects the notional tube to orientate the plate bottom from the original position to the worked position, while retaining the lid in its original orientation; and
 c) engaging the orientated plate bottom with a plate clamping member of a plate platform to clamp the plate bottom.

The plates for use with this invention are likely to be circular, with the lid and bottom therefore defining therebetween a perimetric sidewall. In this form, the notional tube defined above and below the plate is merely a continuation of the partial circular tube formed by the sidewall, continuing indefinitely above and below the plate, and would include that partial circular tube. The tube is notional in that it is an imaginary surface defined as mentioned above for the purposes of defining the present invention. Thus, if the plate were to be, for example, a square shaped plate, the notional tube would be an imaginary surface defined by the continuation of the square sectioned tube formed by four sidewalls, again continuing indefinitely above and below the plate and including the square sectioned tube.

As the held position of the plate is likely to be such that the plate itself is generally horizontal, the notional tube defined by the held position is likely to be a notional vertical tube. Thus, the horizontal axis about which the plate bottom (in the preferred form) is rotated is to intersect this notional vertical tube. In this respect, and to minimize the distance traveled by the plate as it is rotated, and thus to increase the speed of operation of the apparatus, it is envisaged that the axis of rotation will actually intersect the partial tube defined within the lid, the bottom and the side walls of the plate, and will most preferably intersect that partial tube so as to intersect the center or very close to the center (the radial centre for a circular plate) of the plate. In this most preferred form, the plate bottom will then be rotated about its own radial centre (or very nearly about its own radial centre), which is likely to represent the fastest form of orientation of the plate bottom from the original orientation to the worked orientation.

In use, it is most likely that plates will be provided to the orientation mechanism in the inverted orientation mentioned above, which means that a plate's original orientation for the purposes of the apparatus of the present invention will be this inverted orientation, namely with its lid lowermost and its bottom uppermost, and the plate lying generally horizontally. In this form, the opposed jaws will then be an upper jaw and a lower jaw, the upper jaw including the preferred plate-bottom gripping device, the lower jaw including the preferred lid-gripping device, and the notional tube being a notional vertical tube.

In this most preferred form, the jaw support member of the orientation mechanism is not only able to rotate such that the plate bottom rotates about a generally horizontal axis that intersects the notional vertical tube to orientate the plate bottom from its original orientation to its worked orientation (which will preferably be a rotation of 180 degrees and thus an orientation 180 degrees removed from the original orientation), but the jaw support member will also be movable generally vertically such that the plate bottom, ideally at the commencement of the rotation, can be raised slightly away from the lid to release the bottom from the lid in the same continuous motion that then moves into the rotation of the plate bottom down and underneath the retained lid. Once orientated or (more preferably) during orientation, the plate bottom can be lowered onto the plate platform from above (ideally still within the notional vertical tube, as mentioned above) such that the bottom of the plate is moved downwardly to engage with the plate clamping member.

In this respect, it is envisaged that the most preferred form of the present invention will allow for the de-lidding, orientation and lowering of the plate bottom to the platform to occur in one smooth continuous motion.

The de-lidded and orientated plate bottom will then be clamped into the plate platform and the plate platform is then preferably able to be moved horizontally, independently of the other jaw that has retained the lid in its original orientation, away from the notional vertical tube, into some other position (such as a plate work position) where easy access to the medium in the plate can be provided.

As evident from the above, the apparatus of the present invention is primarily suitable for use with an automated streaking apparatus, ideally of the type generally described in the present applicant's international patent application filed on 11 Jan. 2008 titled "Method and Apparatus for Inoculating and Streaking a Medium in a Plate", claiming priority from Australian provisional patent application 2007900146, the full content of which is hereby incorporated by reference. For present purposes, in one form that streaking apparatus generally includes:

(a) a plate supply capable of storing raw plates in an inverted orientation;

(b) a plate transfer feed mechanism capable of obtaining an inverted raw plate (this being the plate's original orientation) from the plate supply, orientating the raw plate such that its bottom is lowermost and it is de-lidded (this being its worked orientation), and transferring the orientated plate bottom to a plate work position in an inoculating and streaking station;

(c) an inoculating device capable of dispensing inoculum on the surface of the medium in the positioned plate;

(d) a streaking device capable of obtaining a streaking applicator from a streaking applicator supply and then moving the streaking applicator such that its line of spaced apart contact surfaces contacts the surface of the medium in the positioned plate, prior to rotation of the positioned plate for streaking;

(e) a plate store capable of storing processed plates in an inverted orientation; and (f) a plate transfer store mechanism capable of retrieving a processed plate from the plate work position, re-lidding and re-orientating the processed plate to its inverted orientation (its original orientation), and transferring the processed plate to the plate store.

Thus, in one form (although not the only form thereof), the apparatus of the present invention is intended to be suitable for use as a part of either or both of the plate transfer feed mechanism and the plate transfer store mechanism in the de-lidding and orientation of a plate, and its subsequent placement in the plate work position in such an automated streaking apparatus.

Turning now to a further description of preferred forms of the orientation mechanism of the present invention, the opposed plate-receiving jaws of the orientation mechanism are preferably configured so as to contact the top and bottom walls of a plate, of course being the lid and bottom mentioned above, as opposed to the perimetric side wall of a plate.

In a preferred form, one or both of the jaws will be retractable such that the jaws can be brought together to clamp a plate therebetween, and one or both of the jaws will include a vacuum-actuated gripping device.

As mentioned above, the plate-receiving jaws are mounted for rotation of at least a plate bottom about a horizontal axis in one of the x or y directions such that the plate bottom can be orientated by 180 degrees about that axis to bring the plate bottom into its worked orientation. In the preferred situation mentioned above, this worked orientation will be the plate's normal, upright (lid upwards) orientation.

Holding the plate bottom in this worked (upright) orientation, the orientation mechanism is able to move to be located over the platform mentioned above, or will already be located over that platform, ideally in a smoothly continuous motion as part of the orientation action. The plate bottom may thus be lowered onto the platform in the same motion as the orientation, ideally to be both centralized upon the platform and clamped thereby. In one form, the jaw holding the plate bottom will be formed from a pair of elongate prongs spaced apart by a distance no larger than the diameter of the bottom of a plate, such that the prongs can be being loosely received within a plate clamping member of the platform such that they are not clamped when the plate is clamped. By then retracting that jaw away from the platform, the plate bottom can be left centralized and clamped upon the platform, in a manner that permits the platform holding the clamped plate bottom to be moved away (if necessary) and into a plate work position, also as mentioned above.

As will be appreciated, the reverse operation then moves the platform, with the clamped plate bottom (after processing and with no lid), out of the plate work position into a position below the retained lid (still in its original position). The plate bottom can then be rotated back up over the lid, to re-join the plate bottom with the lid, such that the plate is returned to its original orientation.

BRIEF DESCRIPTION OF THE DRAWINGS

Having briefly described the general concepts involved with the present invention, a preferred embodiment will now be described that is in accordance with the present invention.

However, it is to be understood that the following description is not to limit the generality of the above description.

In the drawings:

FIG. 1 is a perspective view from above of an apparatus in accordance with a preferred embodiment of the present invention;

FIG. 2 is a perspective view from above of the apparatus of FIG. 1 showing a plate in the held position still in its original orientation;

FIG. 3 is a perspective view from above of the apparatus of FIG. 1 showing the plate bottom being orientated from its original orientation to its worked orientation;

FIG. 4 is a perspective view from above of the apparatus of FIG. 1 showing the orientated plate bottom clamped in a platform in its worked orientation having been de-lidded; and FIG. 5 is a perspective view from above of the apparatus of FIG. 1 showing the orientated and de-lidded plate bottom in a plate work position in an automated streaking apparatus.

DESCRIPTION OF A PREFERRED EMBODIMENT

Figure 1:
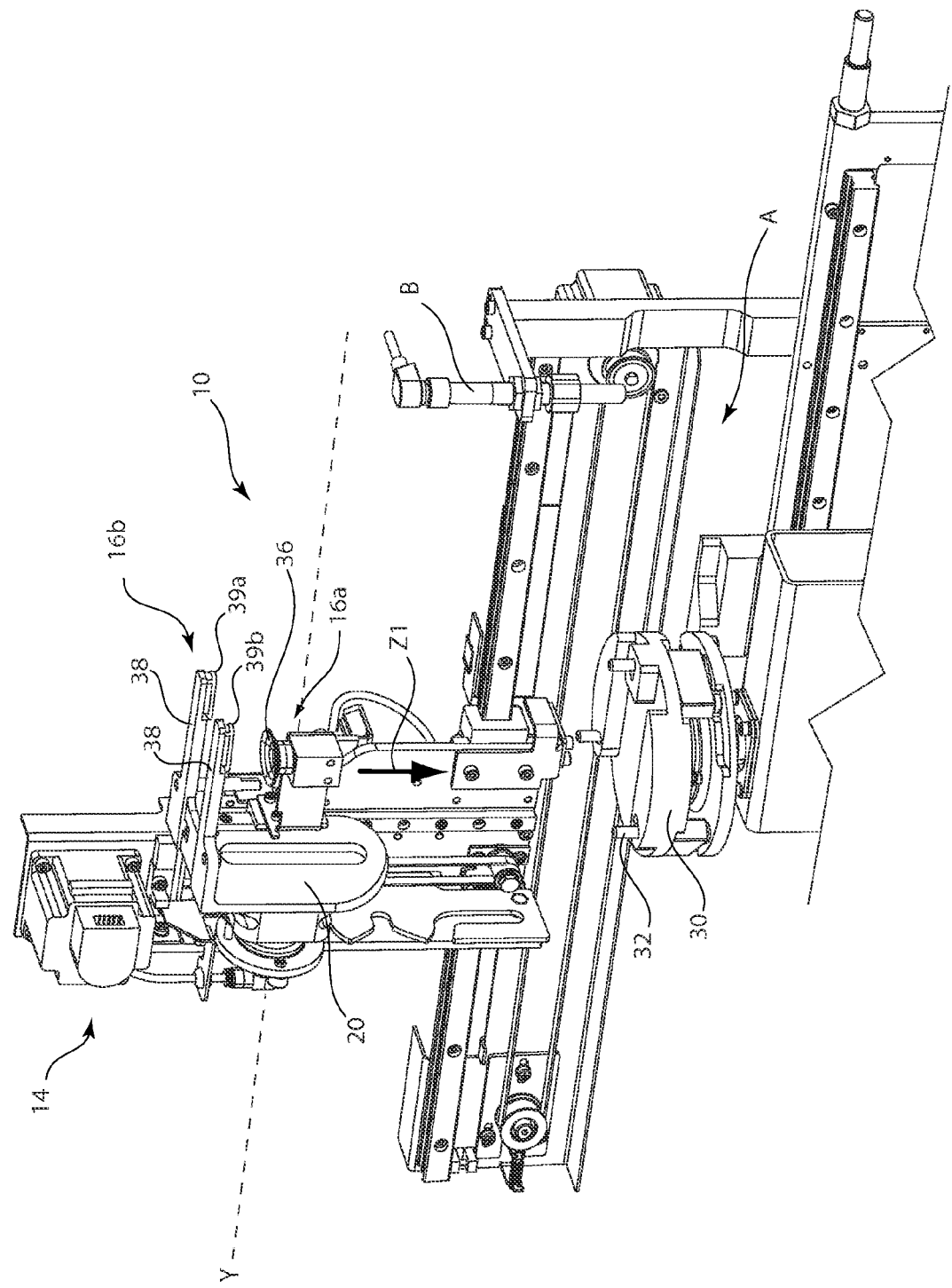
Figure 2:
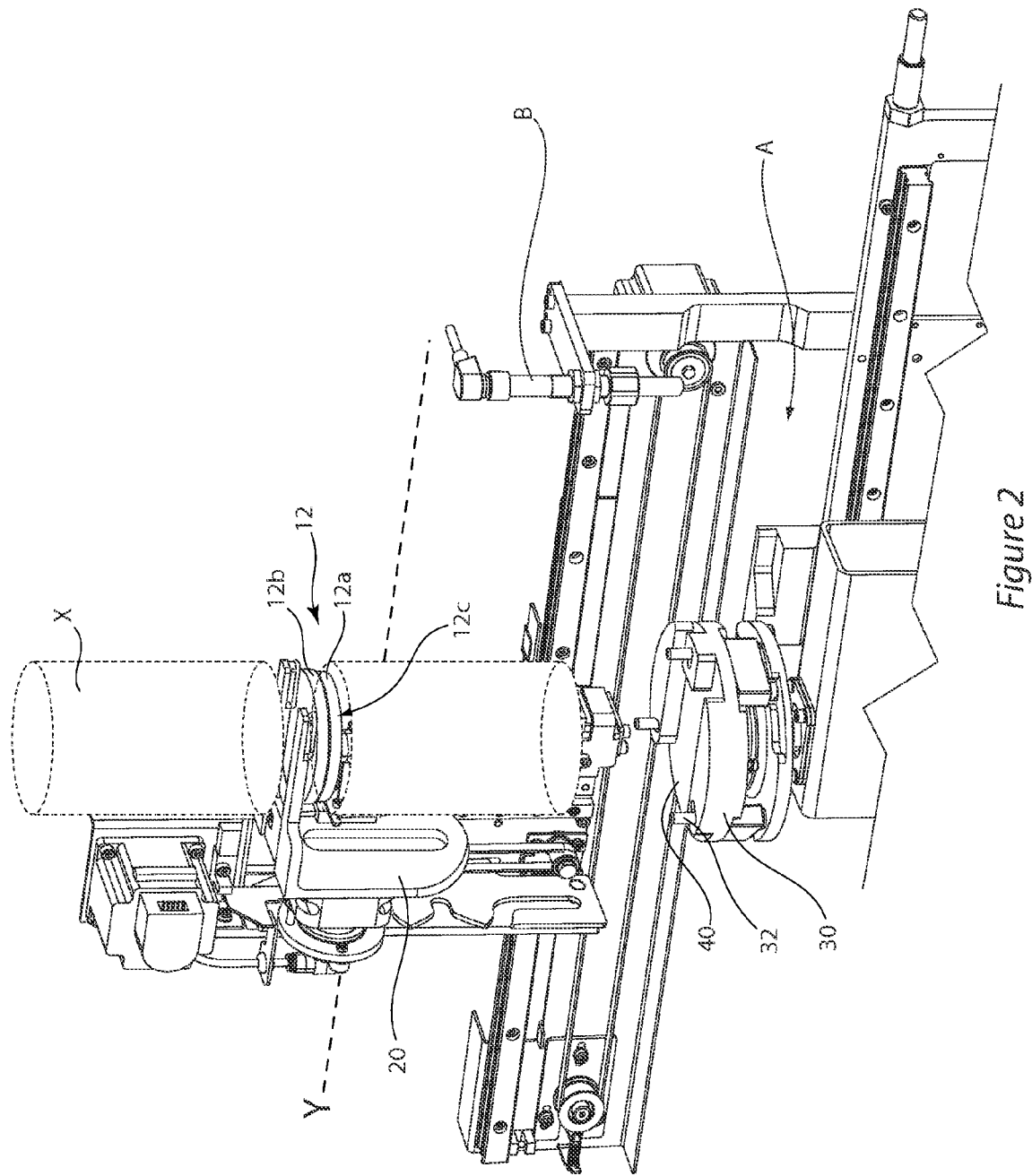
Figure 3:
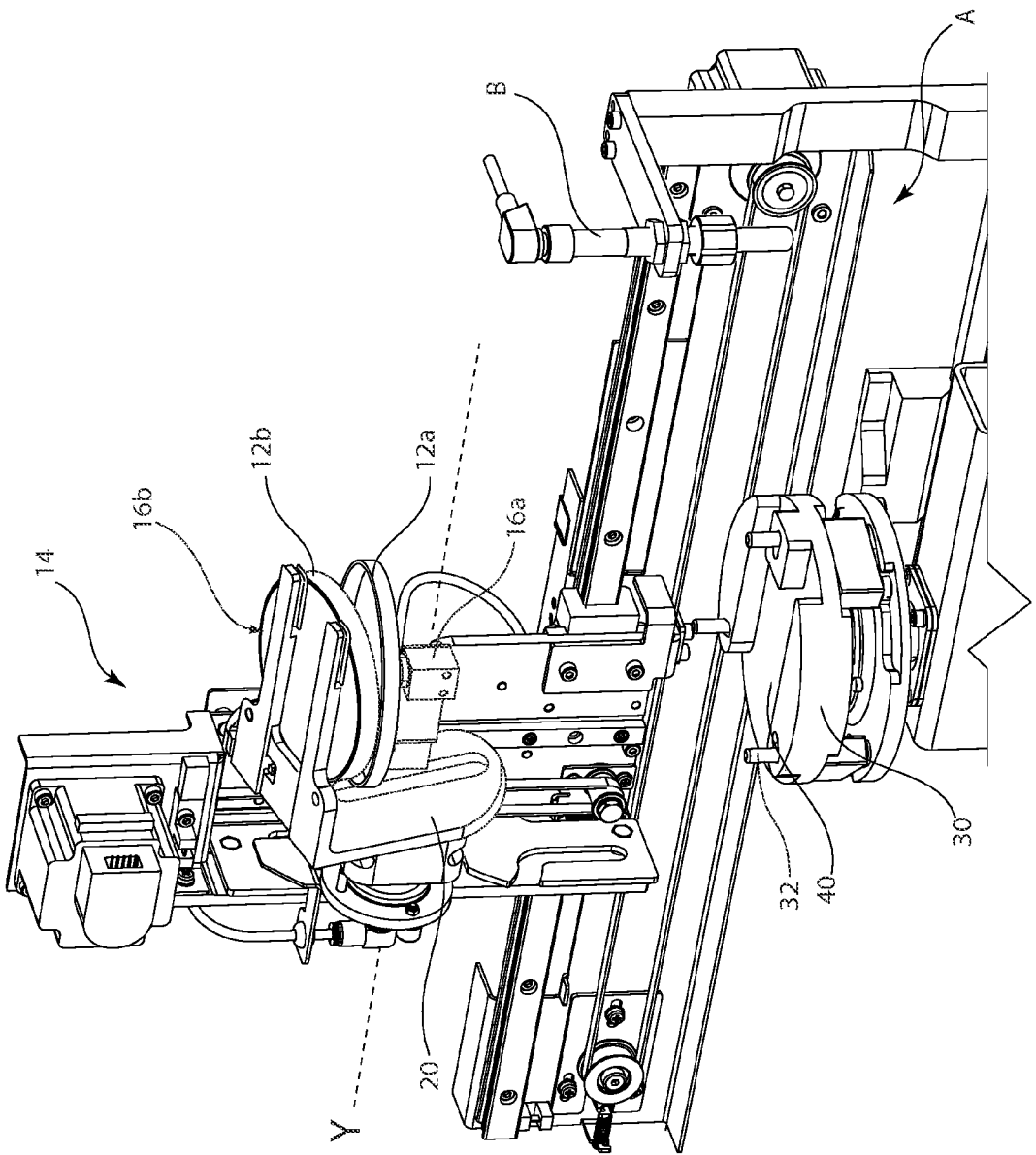
Figure 4:
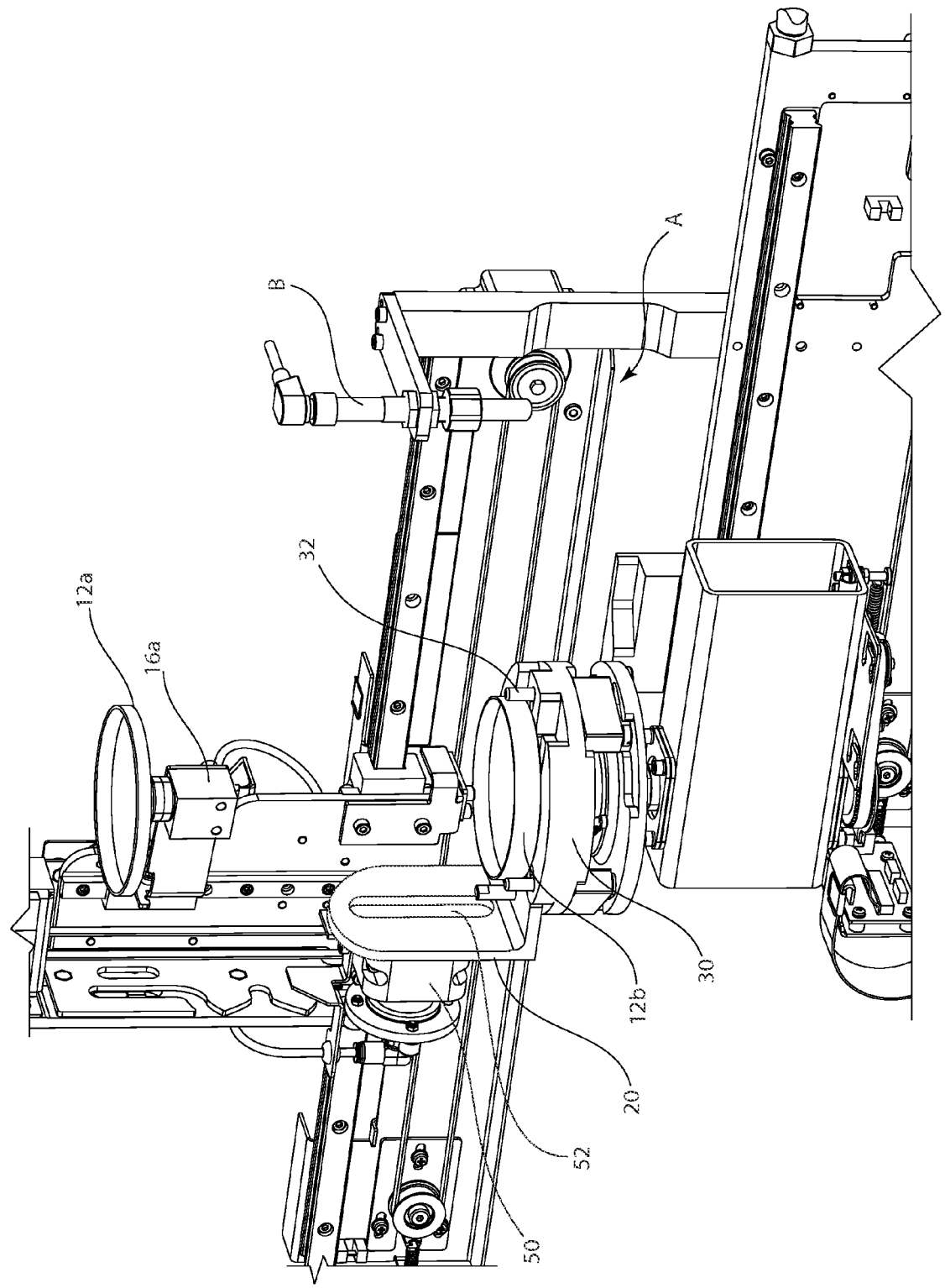
Figure 5:
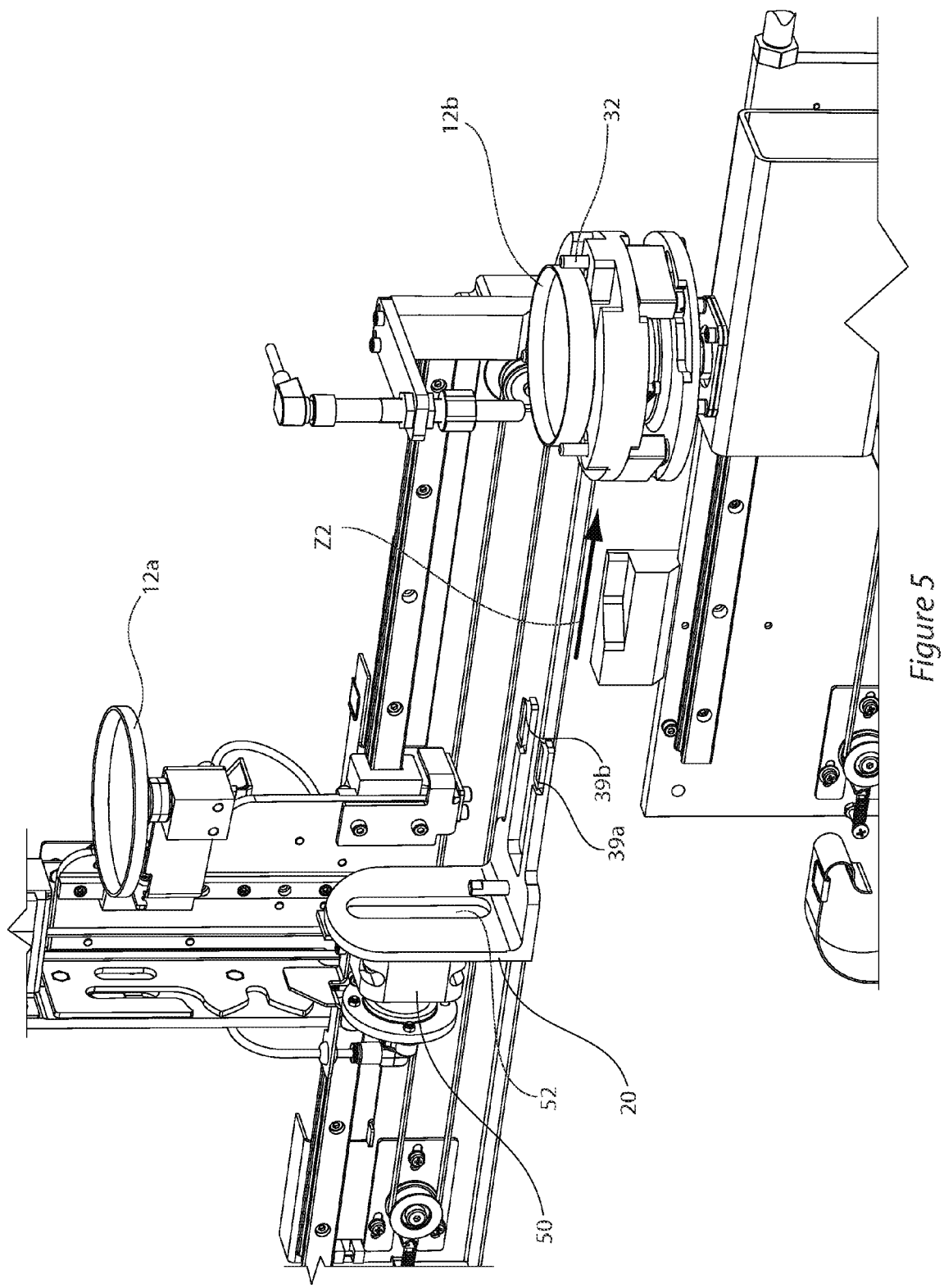

Illustrated in the figures is an apparatus 10 for orientating a solid growth culture medium plate 12 from a held position in an original orientation (shown in FIG. 2) to a worked orientation (shown in FIGS. 3 and 4). FIG. 1 shows the apparatus at rest before a plate 12 (shown in FIGS. 2 to 5) has been placed within it, while FIG. 5 shows the apparatus having been used to orientate and de-lid the plate 12 for subsequent transfer to the plate work position A adjacent a sensor B of an automated streaking apparatus (not shown).

As shown in FIGS. 2 and 3, the plate 12 has a lid 12a and a bottom 12b and, in this embodiment, is a circular plate that has a single perimetric sidewall 12c. Also in this form, the plate 12 is provided to the apparatus in the inverted orientation that is common in most laboratories, namely with the bottom 12b uppermost and the lid 12a lowermost, as is shown in FIG. 2. The apparatus 10 includes an orientation mechanism, generally indicated by the reference numeral 14, that includes opposed jaws (being a lower jaw 16a and an upper jaw 16b when viewed before use and at rest as in FIG. 1) able to receive and hold the plate 12 therebetween.

In this respect, and as shown in FIG. 1, one of the jaws (in this case the lower jaw 16a) is a retractable, vacuum-actuated lid-gripping device 36, the other (the upper jaw 16b) is a pair of retractable elongate prongs 38 spaced apart by a distance no larger than the diameter of the bottom 12b of the plate 12, the upper jaw 16b also including a vacuum-actuated plate-bottom gripping device in the form of vacuum actuated suction caps 39a,39b arranged on respective prongs 38. Thus, when the plate 12 (in its original orientation in FIG. 2) is located between the jaws (16a,16b), relative movement between the upper jaw 16b and the lower jaw 16a is such that the lid-gripping device 36 and/or the plate-bottom gripping device are able to be moved towards the plate 12 to grip and hold the plate 12 therebetween, thereby forming the held position for the plate 12.

When initially placed between the jaws (16a,16b), the plate 12 is held therebetween in a position that is thus defined herein as a "held position". As can be seen from FIG. 2, the held position defines a notional tube X above and below the plate 12, the notional tube X being a continuation of the partial circular tube formed by the sidewall 12c of the plate 12, which continues indefinitely above and below the plate 12. The notional tube X thus includes the partial circular tube formed by the sidewall 12c.

As mentioned above, although the tube has been outlined in FIG. 2 in broken lines, the notional tube is notional in that it is an imaginary surface defined as mentioned above for the purposes of defining the present invention.

The orientation mechanism 14 includes a jaw support member 20 upon which at least one of the opposed jaws (16a,16b) are mounted. In this embodiment, the upper jaw 16b is integral with the support member 20 such that it is retractable and such that the jaw support member 20 is rotatable such that at least the plate bottom 12b rotates about a generally horizontal axis Y that intersects the notional tube X to orientate at least the plate bottom 12b from the original orientation to the worked orientation.

In FIGS. 4 and 5, the jaw support member 20 can be seen mounted to a movable mount 50 that is able to both rotate and move vertically to provide the jaw support member 20 with the range of movement required. In one form, the jaw support member 20 itself may also be configured to move vertically independent of the movable mount 50, thus providing extra ranges of movement if required, perhaps utilizing the central slot 52 and a movable pivot (not shown) therewithin. Indeed, such an arrangement would also provide the jaw support member 20 with a range of movements in the horizontal direction lateral to line y, thus assisting with any required movement of the plate bottom 12b away from the lid 12a as it is rotated off the lid 12a.

FIGS. 4 and 5 also show the mounting of the lower jaw 16a independently of the upper jaw 16b, such that the lower jaw 16a can be retained in its original orientation as the lower jaw 16b (and thus the plate bottom 12b) is raised therefrom and rotated around thereunder during the orientation of the plate bottom 12b from its original orientation to its worked orientation.

It is preferred to locate the horizontal axis Y as close as possible to the radial centre of the plate 12 (or rather to ensure that the plate 12 is held in a position between the jaws (16a, 16b) that is such that the radial centre of the plate 12 is close to the horizontal axis Y), in order to minimize the time for rotation and also the space required within the apparatus to conduct this re-orientation task.

However, in the present embodiment it has been found to be advantageous to space the horizontal axis Y from the radial centre of the plate 12, and indeed to locate that horizontal axis a distance below (in the held position) the lid 12a of the plate 12. In this embodiment, this is due to the preferred retention of the lid 12a in its original orientation and the need to thus slightly raise the plate bottom 12b upwardly and away from the lid 12a and then rotate the plate bottom 12b around the stationary lid 12a, requiring the plate bottom 12b to be moved out of the notional tube X before being returned to within the notional tube X below the lid 12a.

As mentioned above, the aim is then to provide enough space in the apparatus for the plate bottom 12b to be rotated in this manner, whilst still ensuring a short distance of travel for the plate bottom 12b as the orientation is occurring, and then downwardly to the plate platform 30, ideally still generally within the notional tube X. The relative spacings illustrated in the figures have been found to be optimal for the conflicting timing requirements outlined above.

As also mentioned above, the jaw support member 20 of the orientation mechanism 14 is able to rotate such that the plate bottom 12b rotates about a generally horizontal axis Y that intersects the notional tube X to orientate the plate bottom 12b from its original orientation to its worked orientation (which will preferably be a rotation of 180 degrees and thus an orientation 180 degrees removed from the original orientation). However, the jaw support member 20 is also movable generally vertically (in the direction of arrow $Z_1$ in FIG. 1) such that the plate bottom 12b, during orientation or after orientation, can be lowered onto the plate platform 30 from above (still within the notional tube X) in a smoothly continuous motion such that the plate bottom 12b is moved downwardly to engage with a plate clamping member 32, with the prongs 38 being loosely received within a cooperatively shaped channel 40 of the platform 30 such that they are not clamped when the plate 12 is clamped (such as the position shown in FIG. 4).

In this embodiment, the plate clamping member 32 is in the form of three movable lugs operated by a camming device (not shown), which lugs are preferably also able to function as a plate centralizing means for centralizing the position of the plate on the platform 30. This can be useful for subsequent operations with the plate bottom 12b.

Then, in operation, and once the plate bottom 12b is clamped to and centralized in the platform 30, the clamped plate bottom 12b can then be moved away from the prongs 38 horizontally (in the direction of arrow $Z_2$ in FIG. 5), and independently of the orientation mechanism 14, away from the notional tube X and into a plate work position A, where easy access to the medium in the plate bottom 12b can be provided.

As will be appreciated, the reverse operation then moves the platform 30, with the clamped plate bottom 12b (after processing in the plate work position A and with no lid), out of the plate work position A into position back within the notional tube X, where the prongs 38 are again loosely received within the channel 40 of the platform 30 by the plate clamping member 32 of the platform 30 (and are arranged under the plate bottom 12b). The lid 12a can then be re-applied to the plate bottom 12b by slightly raising the plate bottom 12b off the platform 30 and then again rotating the plate bottom 12b, by the jaw support member 20, to be returned to its original orientation in association with the lid 12a.

In conclusion, it must be appreciated that there may be other variations and modifications to the configurations described herein which are also within the scope of the present invention.

We claim:

1. An apparatus for orientating a solid growth culture medium plate from an original orientation to a worked orientation, the plate having a lid and a bottom, the apparatus including:
   an orientation mechanism that includes opposed jaws able to receive and hold a plate therebetween in a held position that defines a notional tube above and below the plate, one of the jaws including a plate-bottom gripping device and being rotatably mounted on a jaw support member such that the plate bottom rotates about a generally horizontal axis that intersects the notional tube to orientate the plate bottom from the original orientation to the worked orientation, the other jaw including a lid-gripping device that retains the lid in its original orientation during rotation of the plate bottom; and
   a plate platform having a plate clamping member able to receive, from the orientation mechanism, the plate bottom in its worked orientation, wherein the original orientation of the plate is an inverted orientation with its lid lowermost and its bottom uppermost.

2. An apparatus according to claim 1, wherein the opposed jaws include (before use and at rest) an upper jaw and a lower jaw, the lower jaw including the lid-gripping device and the upper jaw including the plate-bottom gripping device.

3. An apparatus according to claim 1, wherein either or both of the lower jaw and the upper jaw is a retractable jaw.

4. An apparatus according to claim 1, wherein the jaw support member is movable generally vertically such that the plate bottom, during orientation, can be raised slightly away from the lid at the commencement of rotation to release the plate bottom from the lid, permitting the movement of the plate bottom from the original orientation to the worked orientation to be a smoothly continuous motion generally within the notional tube.

5. An apparatus according to claim 4, wherein either during or after rotation to the worked orientation, the plate bottom can be lowered onto the plate platform to engage with the plate clamping member and, once the bottom is clamped to the platform, the jaw that grips the plate bottom can be retracted away from the clamped bottom plate.

6. An apparatus according to claim 1, wherein the plate platform is able to be moved generally horizontally, independently of the orientation mechanism, such that, once de-lidded, the plate bottom can be moved into another position.

7. An apparatus according to claim 1, wherein the opposed jaws are configured so as to contact top and bottom walls of a plate, as opposed to the perimetric side wall of a plate.

8. An apparatus according to claim 1, wherein the lid-gripping device and the plate-bottom gripping device are vacuum actuated.

9. An apparatus according to claim 8, wherein the jaw having the plate-bottom gripping device includes a pair of elongate prongs spaced apart by a distance no larger than the diameter of a plate.

10. An apparatus according to claim 9, wherein the prongs are able to be loosely received within the plate clamping member such that they are not clamped when the plate is clamped.

11. An apparatus according to claim 1, wherein the axis of rotation intersects a partial notional tube defined within the lid, the bottom and side walls of the plate.

12. An apparatus according to claim 11, wherein the axis of rotation intersects the partial notional tube so as to intersect the radial centre of a circular plate.

13. A method for orientating a solid growth culture medium plate from an original position to a worked position, the plate having a lid and a bottom, the method including the steps of:
   a) clamping a plate in its original position between opposed jaws, one of the jaws including a plate-bottom gripping device rotatably mounted on a jaw support member of an orientation mechanism, thus forming a held position that defines a notional tube above and below the plate, the other jaw including a lid-gripping device;
   b) rotating the plate bottom about a generally horizontal axis that intersects the notional tube to orientate the plate bottom from the original position to the worked position, while retaining the lid in its original orientation; and
   c) engaging the orientated plate bottom with a plate clamping member of a plate platform to clamp the plate bottom,
   wherein the original orientation is an inverted orientation, namely with its lid lowermost and its bottom uppermost.

14. A method according to claim 13, wherein the jaw support member is movable generally vertically such that step (b) includes lowering the clamped plate onto the platform downwardly in a smoothly continuous motion, to be both centralized upon the platform and clamped thereby, by lowering the jaw support member generally within the notional tube.

15. A method according to claim 13, wherein the lid-gripping device and the plate-bottom gripping device are both vacuum-actuated devices.

16. A method according to claim 15, wherein, during step (c), the prongs are loosely received within the plate clamping member of the platform such that they are not clamped when the plate is clamped.

17. A method according to claim 15, including the step of (e) moving the platform such that the clamped and de-lidded plate bottom moves away from the prongs and into a plate work position.

18. A method according to claim 17, the method including the reverse operation of moving the platform, with the clamped plate bottom, out of the plate work position into a lidding position, where the prongs are loosely received by the plate clamping member of the platform, raising the plate bottom of the platform and rotating the plate bottom back to its original orientation to re-lid the plate.

19. A method according to claim 13, wherein the axis of rotation intersects a partial notional tube defined within the lid, the bottom and side walls of the plate.

20. A method according to claim 19, wherein the axis of rotation intersects the partial notional tube so as to intersect the radial centre of a circular plate.

21. A method for orientating a solid growth culture medium plate from an original orientation to a worked orientation, the plate having a lid and a bottom, the method including the steps of:
   a) clamping a plate in its original orientation between opposed jaws mounted on a jaw support member of an orientation mechanism, thus forming a held position that defines a notional tube above and below the plate; and
   b) rotating at least the plate bottom about a generally horizontal axis that intersects the notional tube to orientate at least the plate bottom from the original orientation to the worked orientation,
   wherein the original orientation is an inverted orientation, namely with its lid lowermost and its bottom uppermost.

* * * * *